(12) United States Patent
Yamashina et al.

(10) Patent No.: US 6,569,840 B1
(45) Date of Patent: May 27, 2003

(54) LOW-MOLECULAR HEPARIN MODIFICATION AND REMEDY FOR SKIN ULCER

(75) Inventors: Ikuo Yamashina, 2, Higashi Morigamae-Cho, Shimogamo, Kyoto (JP), 606-0866; Minoru Okayama, Kyoto (JP); Ken-ichi Toda, Kyoto (JP)

(73) Assignee: Ikuo Yamashina, Kyoto (JP)

( * ) Notice: Subject to any disclaimer, the term of this patent is extended or adjusted under 35 U.S.C. 154(b) by 0 days.

(21) Appl. No.: 09/554,018

(22) PCT Filed: Nov. 18, 1998

(86) PCT No.: PCT/JP98/05191

§ 371 (c)(1),
(2), (4) Date: May 9, 2000

(87) PCT Pub. No.: WO99/26984

PCT Pub. Date: Jun. 3, 1999

(30) Foreign Application Priority Data

Nov. 20, 1997 (JP) .............................................. 9-319997

(51) Int. Cl.[7] ...................... A61K 31/727; C08B 37/10; C07H 5/04; C07H 5/06
(52) U.S. Cl. .......................... 514/56; 536/21; 536/55.3; 536/55.1
(58) Field of Search .............................. 514/56; 536/21, 536/55.3, 55.1

(56) References Cited

U.S. PATENT DOCUMENTS

| | | | |
|---|---|---|---|
| 4,757,057 A | 7/1988 | Fussi et al. | 514/56 |
| 4,990,502 A | 2/1991 | Lormeau et al. | |
| 5,037,810 A | 8/1991 | Saliba, Jr. | |
| 5,280,016 A | * 1/1994 | Conrad et al. | 514/56 |
| 6,001,820 A | * 12/1999 | Hirsh et al. | 514/56 |

FOREIGN PATENT DOCUMENTS

| | | |
|---|---|---|
| JP | 57180604 | 11/1982 |
| JP | 62-4703 | 1/1990 |
| WO | WO9202232 | 2/1992 |
| WO | WO9217187 | 10/1992 |
| WO | WO9629973 | 10/1996 |
| WO | WO9814481 | 4/1998 |

* cited by examiner

*Primary Examiner*—Raymond Henley, III
(74) *Attorney, Agent, or Firm*—Varndell & Varndell, PLLC

(57) ABSTRACT

The invention is direct to modified heparins, especially low-molecular weight modified heparins that are adapted for used in preparing an agent for treating a skin ulcer. The low-molecular weight modified heparins have been substantially deprived of the anticoagulant activity, yet they retain the ability to bind to cell growth factors, cytokines and cell adhesion molecules.

10 Claims, 6 Drawing Sheets

LOW-MOLECULAR HEPARIN MODIFICATION AND REMEDY FOR SKIN ULCER

This is a 371 of PCT/JP98/05191 filed Nov. 18, 1998.

FIELD OF THE INVENTION

This invention relates to modified heparins and an agent for remedying skin ulcer. More particularly, this invention relates to using as an agent for remedying skin ulcer modified heparins, especially low molecular weight modified heparins which have been substantially deprived of the anticoagulant activity yet retain the ability to bind to cell growth factors, cytokines and cell adhesion molecules, and also relates to modified heparins, especially low molecular weight modified heparins adapted for use in preparing an agent for remedying skin ulcer.

BACKGROUND OF THE INVENTION

Heparin is one of glycosaminoglycans and is characterized by having anticoagulant activity. A lot of heparin has been found in liver, lung, intestine, spleen and other organs of healthy edible animals, and heparin is largely produced by mast cells around capillary vessels. A heparin is glycosaminoglycan including various amounts of O-sulfate, N-sulfate and N-acetyl groups and belongs to a heteropolysaccharide having a molecular weight of 6,000~20,000.

More particularly, heparin is formed by a combination of ten kinds of disaccharide having chemical formulas shown in the following Table 1.

TABLE 1

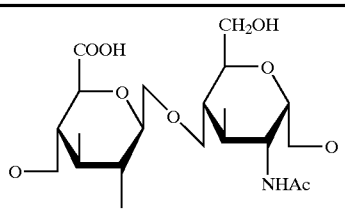

GlcA-GlcNAc

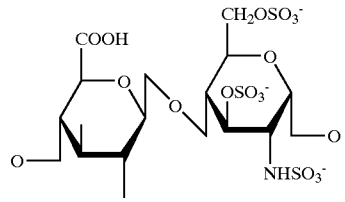

GlcA-GlcNS(3,6diOS)

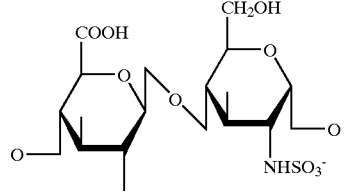

GlcA-GlcNS

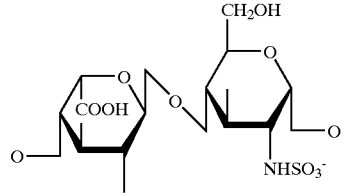

IdA-GlcNS

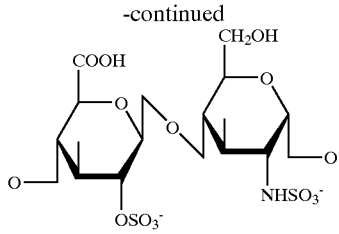

GlcA(2OS)-GlcNS

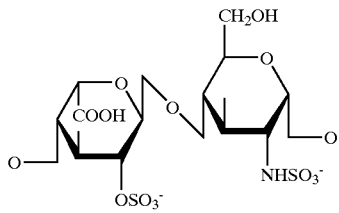

IdA(2OS)-GlcNS

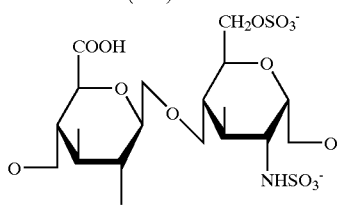

GlcA-GlcNS(6OS)

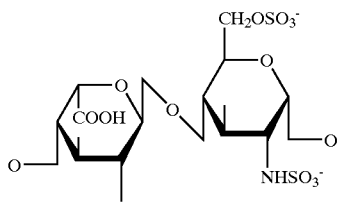

IdA-GlcNS(6OS)

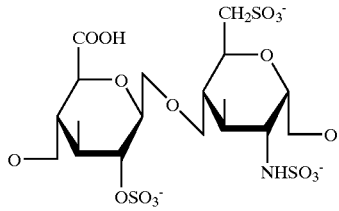

GlcA-(2OS)-GlcNS(6OS)

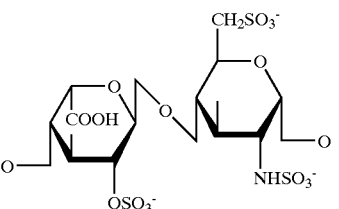

IdA-(2OS)GlcNS(6OS)

In the Table, GlcA denotes D-glucuronic acid, GlcNAc N-acetyl-D-glucosamine, GlcNS N-sulfo-D-glucosamine, GlcA (2OS) 2-sulfo-D-glucuronic acid, GlcNS(6OS) N-sulfo-D-glucsamine-6-sulfate, GlcNS(3,6diOS) N-sulfo-D-glucosamine-3,6-disulfates, IdA L-iduronic acid, IdA (2OS) 2-sulfo-L-iduronic acid, respectively.

Heparin exhibits a variety of biological activities. Namely, heparin binds to a wide variety of cell growth factors, cytokines and cell adhesion molecules. The major function of heparin is that it binds to enzymes and factors such as antithrombin HI involved in blood coagulation and fibrinolysis, thus inhibiting blood coagulation as mentioned above.

It has never been anticipated that heparin itself is effective in remedying skin ulcer. It is because, when heparin is applied on the skin ulcer, it would promote hemorrhage due to its inherent anticoagulant property, and accordingly it would be liable to worsen conditions of the skin ulcer.

Some trials have been made to make use of heparin as a drug by depolymerizing heparin to form low molecular weight heparin or by chemically modifying heparin. For example, JP30277/1979 discloses that heparin can be used as an agent for remedying thrombosis when heparin is depolymerized to form low molecular weight heparin having molecular weights of 2,000–5,000, and the resultant product is then chemically modified.

WO80/01383 discloses that a low molecular weight heparin having a selective anticoagulant activity can be obtained which has a weakened anti-thrombotic activity and a strengthened anti-factor Xa activity, when heparin is treated with nitrite, or oxidized with periodate, and the resultant product is subjected to β-elimination reaction with alkali.

JP66192/1988 discloses that heparin-typed oligosaccharides having an affinity to cell growth factors and showing specific nuclear magnetic resonance spectra can be used for remedying muscle and blood vessel diseases.

WO88/06840 discloses that heparin can be used for preserving and restoring cells when heparin is kept in an appropriate concentration.

U.S. Pat. No. 5,280,016 discloses that a heparin derivative obtained by oxidizing heparin with periodate without depolymerizing heparin and then by reducing the oxidized heparin with borohydride can be used as a drug for injection for inhibiting proliferation of muscle cells.

U.S. Pat. No. 5,296,471 discloses that a heparin derivative obtained by removing 2-O-sulfate and/or 3-O-sulfate groups from heparin to various degrees can be used for preventing and remedying various deseases such as cancer.

JP505179/1995 discloses that when heparin is depolymerized chemically or enzymatically to form various oligosaccharides, which are then divided into various fractions according to properties binding to cell growth factors, thus divided fractions can be used for an agent for adjusting growth of specific cells.

WO96/29973 discloses that, when heparin is depolymerized with nitrite to form low molecular weight heparin, which is then oxidized with periodate, and thereafter the resultant product is further reduced with borohydride, a low molecular weight modified heparin can be obtained which has no anticoagulant activity, and the said modified heparin can be used as a drug for injection for preventing thrombus formation.

WO98/14481 discloses that, when heparin is depolymerized with nitrite to form low molecular weight heparin, which is then oxidized with periodate, and thereafter the resultant product is further reduced with borohydride, a low molecular weight modified heparin can be obtained which has no anticoagulant activity, and the said modified heparin can be used for remedying diseases such as kidney malfunction and myocardial infarction.

As mentioned above, it is known that heparin is depolymerized to form a low molecular weight heparin, the low molecular heparin or heparin itself is chemically modified to form modified derivatives, and the modified derivatives are used for a drug. However, the drug is mainly for use in injection, and is used exclusively for remedying diseases of visceral organs such as heart and kidney.

SUMMARY OF THE INVENTION

The invention is directed to an agent for treating a skin ulcer. The agent can be a modified heparin, especially a low-molecular weight modified heparin. A typical agent in accordance with the present invention is a low-molecular weight modified heparin that has been substantially deprived of its anticoagulant activity, but retains its ability to bind to cell growth factors, cytokines and cell adhesion molecules.

DISCLOSURE OF THE INVENTION

Figure 1:
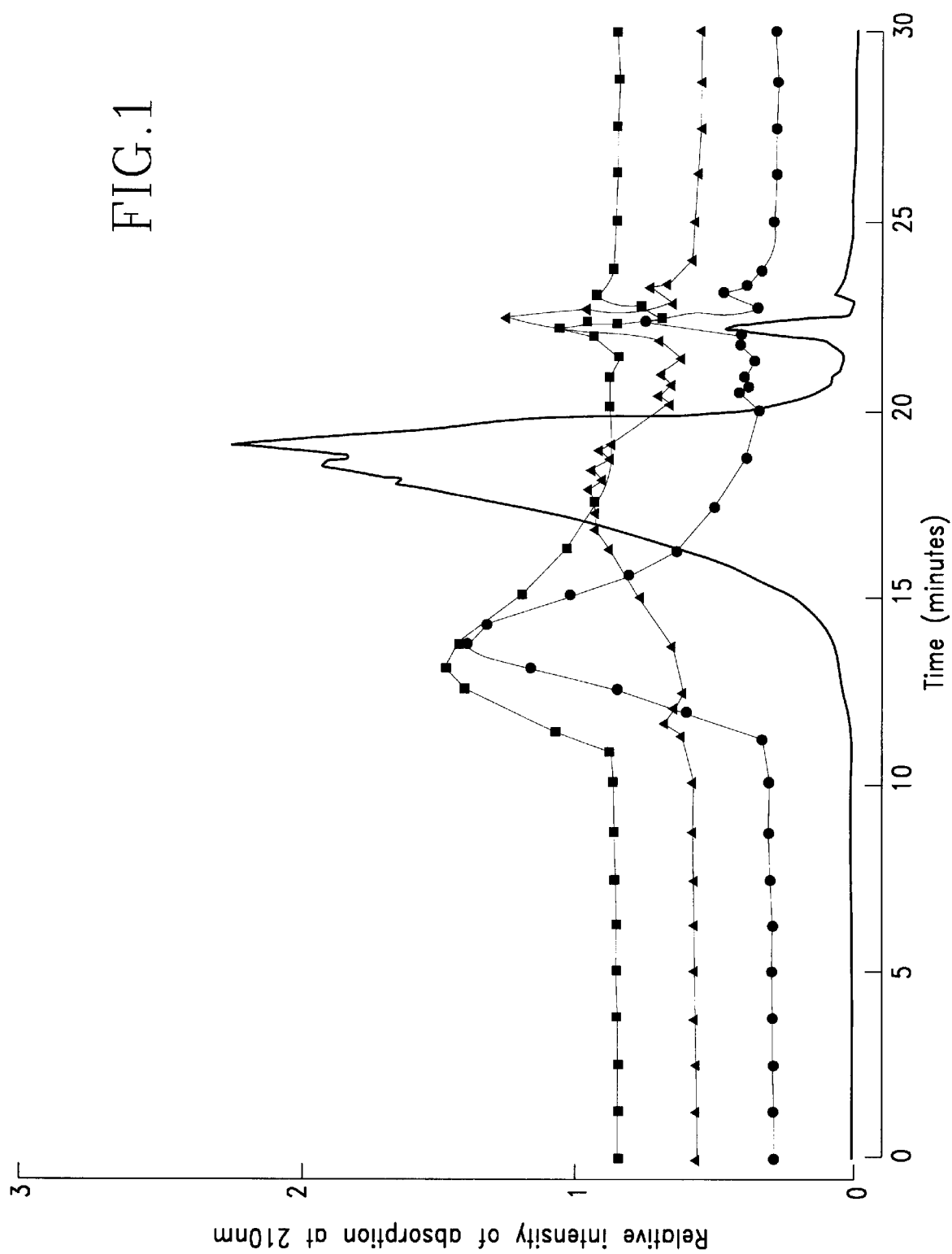
FIG. 1 shows properties of the compounds of the present invention, reference examples, and heparin.

The inventors thought that, if heparin could be modified so as to eliminate or minimize the anticoagulant and antithrombotic activities inherent to heparin, while it maintains the ability to bind to cell growth factors, cytokines and cell adhesion molecules, then the resultant modified heparin would exhibit excellent effects for remedying wounds and decubitus ulcer.

On the basis of above ideas, the inventors tried to modify heparin by oxidizing heparin with periodate, then reducing the resultant product with borohydride to prepare a modified heparin, and thereafter depolymerizing chemically the modified heparin so as to have an average molecular weight of about 1,500–8,000, and as the result the inventors have found that thus obtained low molecular weight modified heparin has lost the anticoagulant activity, however, retains the ability to bind to cell growth factors, cytokines and cell adhesion molecules.

Thus, the inventors mixed the low molecular weight modified heparin with appropriate base materials to prepare an ointment and applied the ointment on the skin ulcer portion of a patient, and observed the progress of the skin ulcer. As the result, the inventors have found that the ointment exhibits an excellent remedying effect, especially an excellent remedying effect for decubitus ulcer. Relying on this finding, the inventors further studied and have come to complete this invention.

This invention makes it an essential feature that a specific modified heparin is prepared by chemically modifying heparin so as to diminish or minimize the anticoagulant activity inherent to heparin, without degrading the ability to bind to cell growth factors, cytokines or cell adhesion molecules inherent to heparin, and that the specific modified heparin is used as an agent for remedying skin ulcer. Also the invention provides a low molecular weight modified heparin adapted for use in the agent for remedying skin ulcer.

The term, the ability to bind to cell growth factors, cytokines and cell adhesion molecules possessed by heparin, used herein means the abilities, for example, the ability to regulate activities toward immune response, to exhibit ulcer healing activities, anti-virus activities, regulatory activities toward cell proliferation and differentiation, to have interactions with proteinous factors intermediating cell-cell interactions and binding to cytokines and cell adhesion molecules, and further to strengthen (or weaken in some cases) activities of these factors. As examples of the proteinous factors may be given interferon γ, interleukins, tumor necrotic factors, lymphotoxing, colony stimulating factors, epidermal growth factors, fibroblast growth factors, transforming growth factor β, endothelial cell growth factors, hepatocyte growth factors, laminin and fibronectin.

The term, anticoagulant activity, used herein means the activity of inhibiting blood coagulation. The anticoagulant activity can be indicated by antithrombotic activity, which may be measured by APTT (Activated Partial Thromboplastin Time), and also by anti-factor Xa activity, which can be measured by specific assay for anti-factor Xa activity. Methods for measuring these activities are fully explained, for example, by T. W. Barrowcliffe in his statements (Heparin assays and standardization in Heparin, D. A. Lane and U. Lindahl ed. Edward Arnold, 1989, P.393–415), by which the anticoagulant activity can be known.

Figure 2:
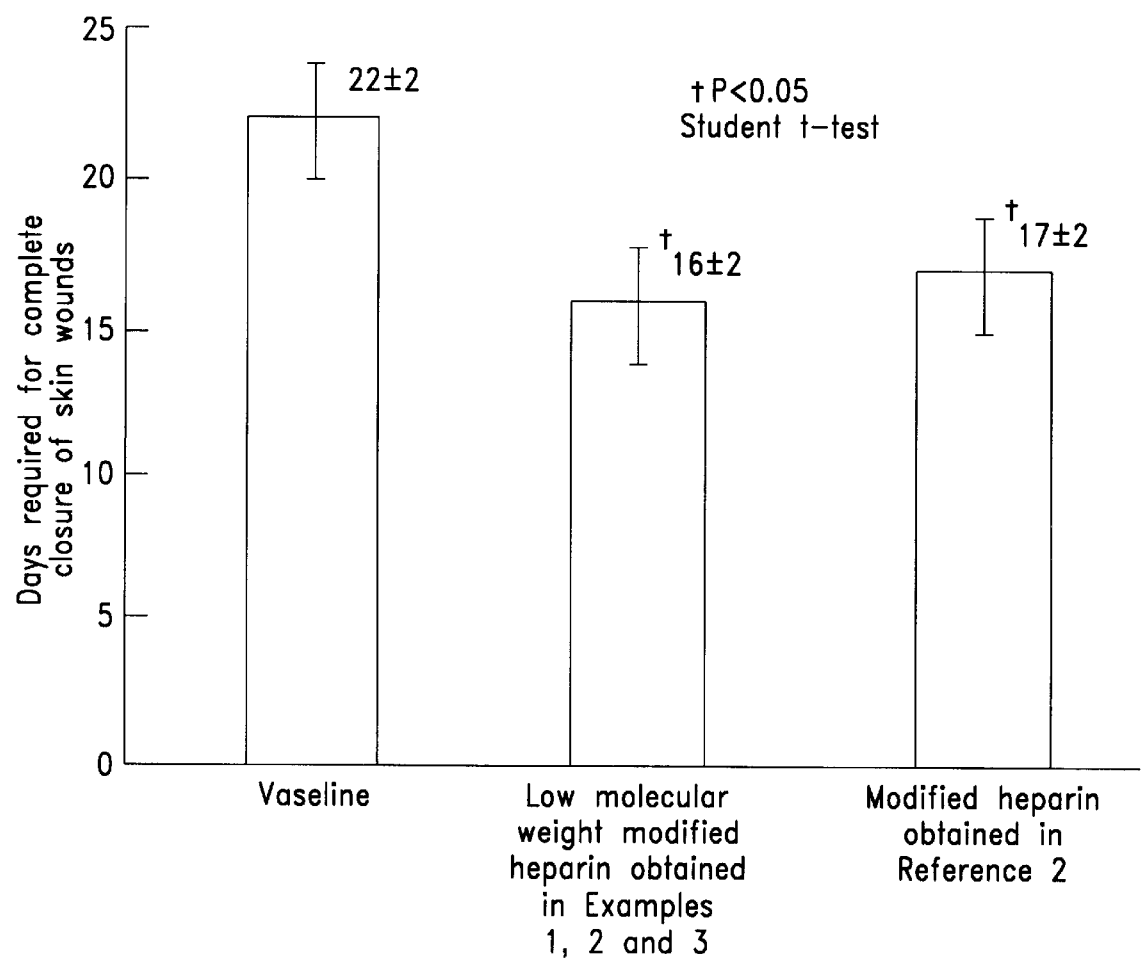
FIG. 2 shows healing properties of the compounds of the present invention and reference examples.
Figure 3:
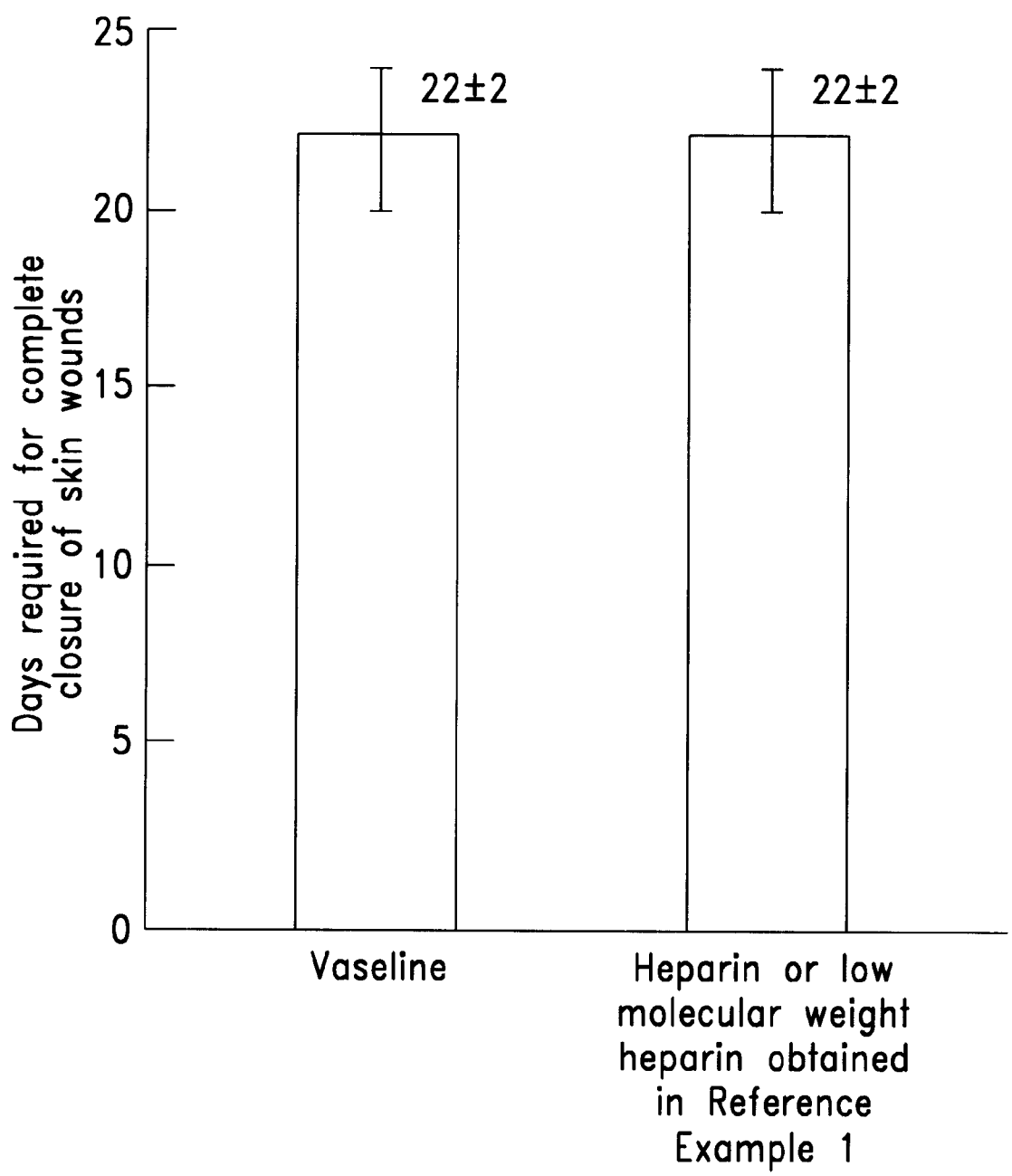
FIG. 3 shows healing properties of the compounds of the present invention, heparin and Vaseline.
Figure 4:
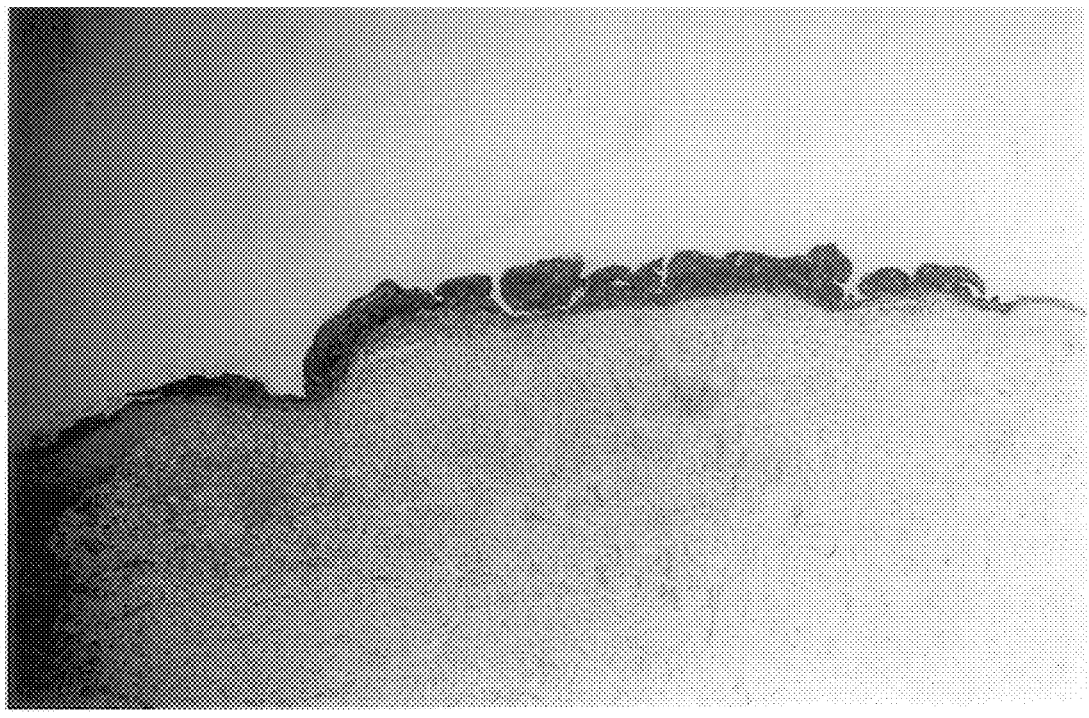
FIG. 4 is a microphotograph of a stained tissue specimen after it has been treated with Vaseline.
Figure 5:
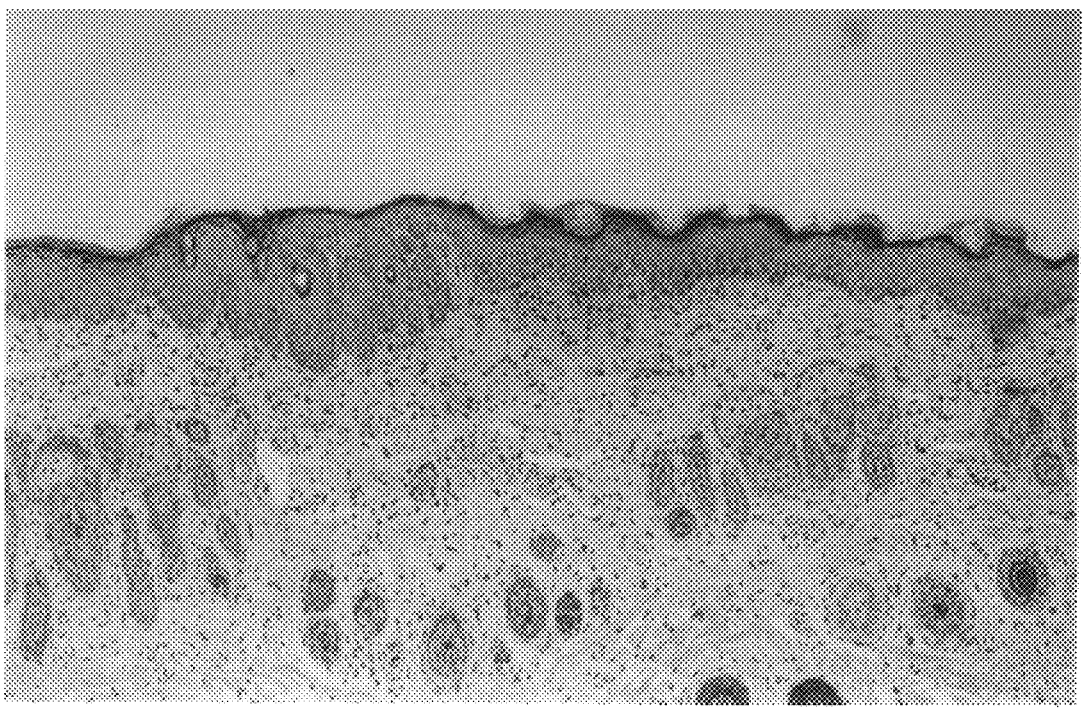
FIG. 5 is a microphotograph of a stained tissue specimen after it has been treated with the compounds according to the present invention.
Figure 6:
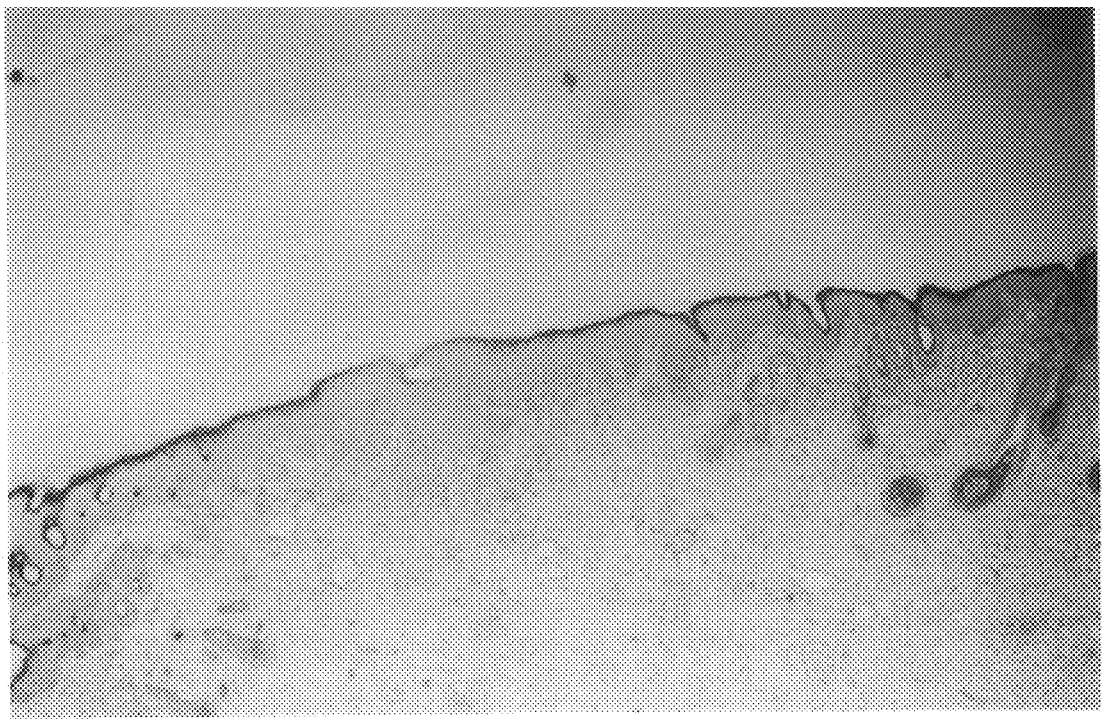
FIG. 6 is a microphotograph of a stained tissue specimen after it has been treated with the reference compound.

The invention will be fully described hereunder, in which FIG. 1 shows results of analysis of the compounds obtained in Example 1, Example 2, Example 3, Reference Example 1 and Reference Example 2 compared with heparin by High Performance Liquid Chromatography (HPLC); FIG. 2 shows comparison of days required for remedying skin ulcer in Experiment 1 using the compounds obtained in Example 1, Example 2, Example 3 and Reference Example 2; FIG. 3 shows comparison of days required for remedying skin ulcer in Experiment 2 using vaseline, heparin and the compounds obtained in Reference Example 1; FIG. 4 shows a microphotograph of a stained tissue specimen after it has been treated with vaseline alone for 11 days in Experiment 1; FIG. 5 shows a microphotograph of a stained tissue specimen after it has been treated with the compounds obtained in Examples 1, 2 and 3 for 11 days in Experiment 1; and FIG. 6 shows a microphotograph of a stained tissue specimen after it has been treated with the compound obtained in Reference Example 2 for 11 days in Experiment 2.

In the invention, use for remedying skin ulcer may be made of a modified heparin obtained by modifying heparin, or a low molecular weight modified heparin obtained by depolymerizing heparin and modifying the resultant low molecular weight heparin. The depolymerization and modification may be carried out in either order. The low molecular weight modified heparin may be one which is prepared by chemically modifying low molecular weight heparin available in the market, or one which is prepared by at first chemically modifying heparin, and then depolymerizing the resultant modified heparin.

In the invention, a method was adopted for preparing the low molecular weight heparin, in which heparin was at first chemically modified to lose and forfeit the blood coagulating property, and thereafter the resultant product was depolymerized to form low molecular weight compounds. For chemical modification was used the conventional method in which heparin was oxidized at first with periodate, and then the resultant product was reduced with borohydride. As is well known, the periodate attacks generally a portion including vicinal hydroxyl groups, or an aminoalcohol portion to form two aldehyde groups (For example, L.-A. Fransson et al., Carbohydr. Res.,80, 131–145, 1980). When periodate is reacted with heparin, hexuronic acid residues (glucuronic acid and iduronic acid) having no sulfate group included in heparin are oxidized, as shown by chemical formulas in Table 2. Degree of oxidation is dependent on concentration of reagents, pH, temperature and time when the reaction is carried out.

TABLE 2
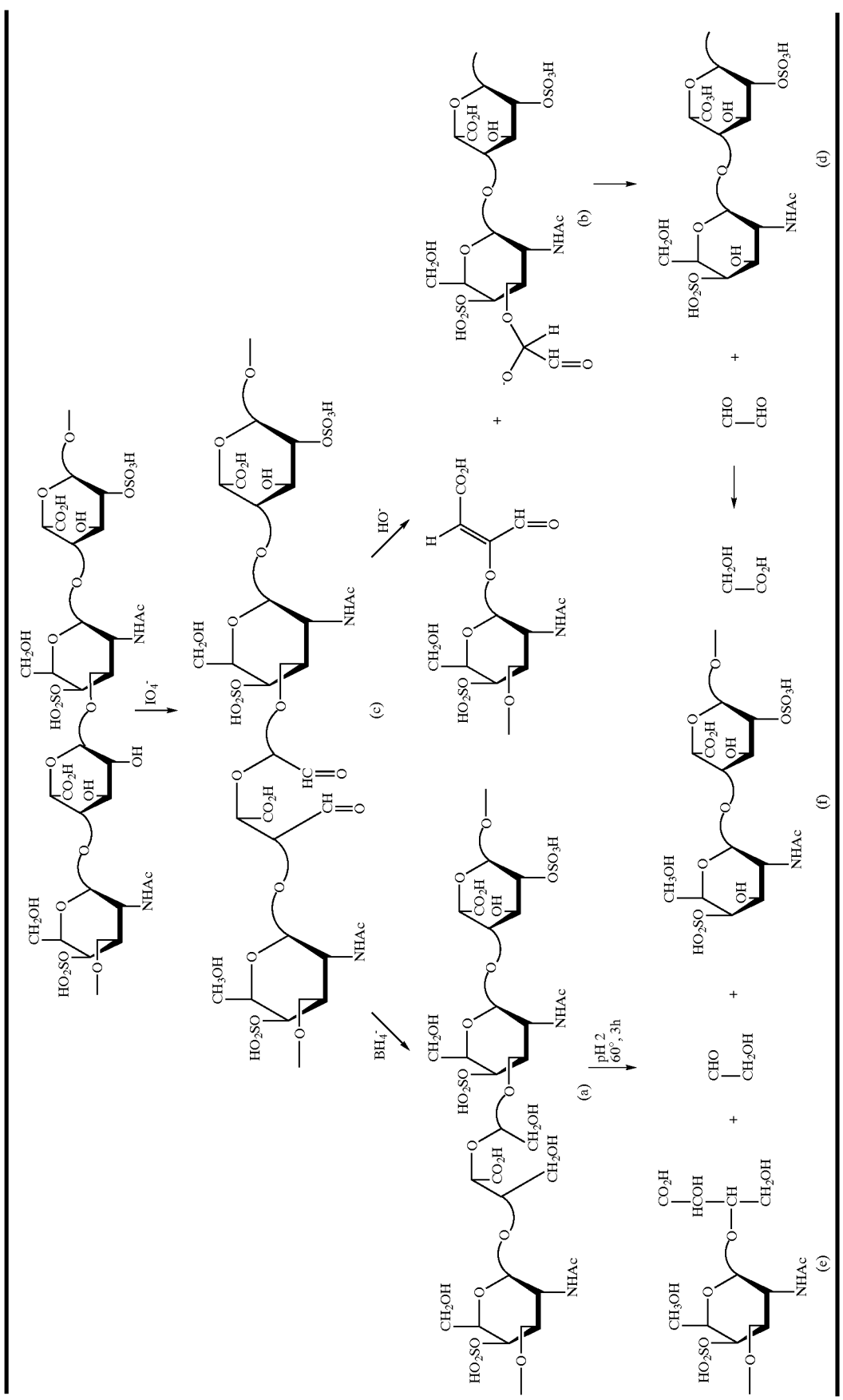

When oxidation is carried out with periodate, pH is critical. At low pH such as 3, iduronic acid residues are preferentially oxidized, however, at high pH such as more than about 5, glucuronic acid residues are also oxidized. In order to eliminate anticoagulant activity of heparin, glucuronic acid residue should be oxidized, and in the invention pH is maintained at 3~6, preferably 5. Thus, compound (c) shown in Table 2 can be obtained, which has aldehyde groups. When the compound (c) is further reduced with borohydride, compound (a) shown in Table 2 can be obtained. The compound (a) has no blood coagulant activity (B. Basu et al. Arzneim. -Forsh./Drug Res., 36, 637–642, 1986). The compound (a) is disclosed in U.S. Pat. No. 5,280,016.

In Table 2, oxidation and reduction are shown in respect of iduronic acid, which is taken as an example, and these reactions can be carried out in the same manner as for glucuronic acid. The heparin modification represented by chemical formula (a) is depolymerized to form low molecular weight compounds under acidic conditions, and the low molecular weight compounds having appropriate molecular weights can be obtained by controlling pH, temperature and reaction time. Both modified heparins represented by chemical formulas (a) and (c) have an activity for remedying skin ulcer, however, it is found that the activity is inferior to that of low molecular weight modified heparin prepared by depolymerizing the modified heparin.

On the other side, the compound (c) produced by periodate oxidation undergoes β-elimination reaction to form low molecular compound (b) as shown in Table 2 under the strong alkaline conditions, and the compound (b) is further decomposed. Thus obtained low molecular weight modified heparin (d) can be also used for an agent for remedying skin ulcer.

As mentioned above, both modified heparins shown by chemical formulas (a) and (c) can be used for an agent for remedying skin ulcer. However, these modified heparins, when compared with their depolymerized ones, are inferior in the effects for remedying ulcer as already mentioned above.

In the invention, the modified heparin shown by the chemical formula (a) in Table 2 is further depolymerized to form low molecular weight modified heparins (e) and (f), which retain the ability to bind to cell growth factors, cytokines and cell adhesion molecules, and which forfeit substantially anticoagulant activity.

For chemical depolymerization of heparin may be used various methods which include hydrolysis, deaminative degradation, oxidative degradation with periodate, oxidation and reduction induced by radicals, degradation with sulfuric acid and degradation by elimination reaction (K. Nagasawa, Carbohydrate Technology, Kabushiki Kaisha Sangyo Chohsakai, Biotechnology Information Center, August 1992, P.315–342).

In the invention, hydrolysis and deaminative degradation are adopted for degradation to form low molecular weight compounds. By either of these procedures, satisfactory results can be obtained if the procedures are advanced under properly controlled conditions.

The hydrolysis is carried out under acidic conditions, for example, the hydrolysis can be completed in 3 hours if pH and temperature are maintained at 2 and 60° C., respectively. Thus, as shown in the left lower part in Table 2, the compound (a) can be cleaved ultimately at the site of every hexuronic acid. Therefore, when the hydrolysis is stopped at an appropriate point by shortening the reaction time and/or lowering the reaction temperature, it is possible to obtain low molecular weight modified heparins (e) and (f) having desired average molecular weights.

Thus obtained compound (e) has at its end L-threonic acid, which is an aglycon of the aminosugar at the reducing terminal of the compound (e), and the carboxyl group of the L-threonic acid may be further modified by esterification, amidation and so on to form secondarily modified compounds. The secondarily modified compounds are also included in the low molecular weight modified heparins.

The deaminative degradation is carried out as shown in Table 3 using nitrite under acidic conditions. The nitrite reacts with N-sulfate group in aminosugar at low pH to form an unstable N-nitroso compound as an intermediate which then cyclizes intramolecularly to form 2,5-anhydro-D-mannose, and the glycosidic bond of glucosamine is cleaved. Reaction of the nitrite with N-sulfate group of the glucosamine proceeds at the fastest speed at pH 1.5, at gradually decreased speed according as pH is elevated, and is substantially stopped when pH is 4 or higher. Therefore, by controlling concentration (amount) of nitrite, reaction time, pH and reaction temperature, it is possible to obtain a low molecular weight modified heparin having a desired average molecular weight.

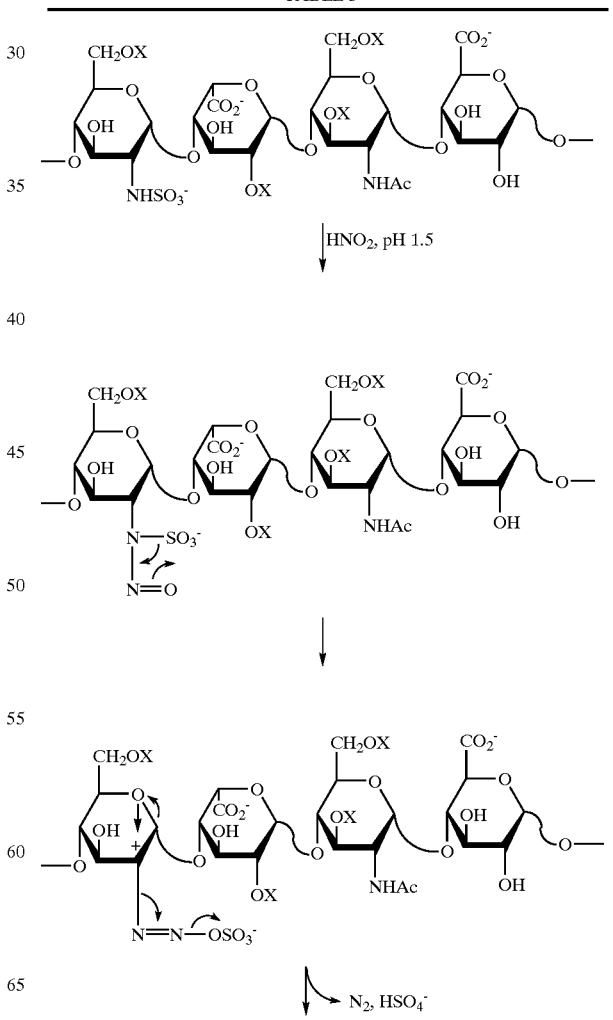

TABLE 3

-continued

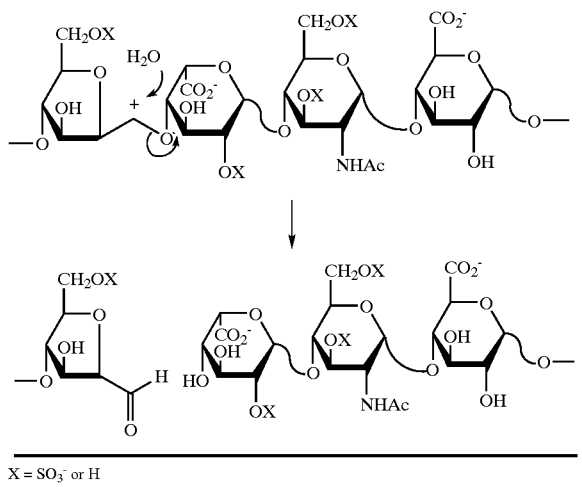

X = SO$_3^-$ or H

The low molecular weight heparin obtained by reacting heparin with nitrite has at its reducing terminal an aldehyde group of 2,5-anhydro-D-mannose, which may be modified chemically in various ways as shown in below Table 4. For example, the aldehyde group may be reacted with compounds having amino group to form a Schiff base. Also the aldehyde group may be reduced to an alcohol group using an equivalent amount of sodium borohydride in a medium of water or alcohol in the presence of sodium bicarbonate at room temperature or under ice chilled conditions. Also the aldehyde group may be oxidized to form a carboxyl group using 1–5 equivalents of active manganese dioxide in a medium of water or alcohol in the presence of Celite. Further thus obtained carboxyl group may be esterified or amidated to produce corresponding ester or amide derivatives, respectively, or the carboxyl group may be subjected to reductive amidating reaction by using borohydride in the presence of amine to produce corresponding various aminomethyl derivatives. These secondarily modified heparins obtained from the modified heparin have good effect for remedying skin ulcer. The secondarily modified heparins, therefore, are included in the low molecular weight modified heparin.

TABLE 4

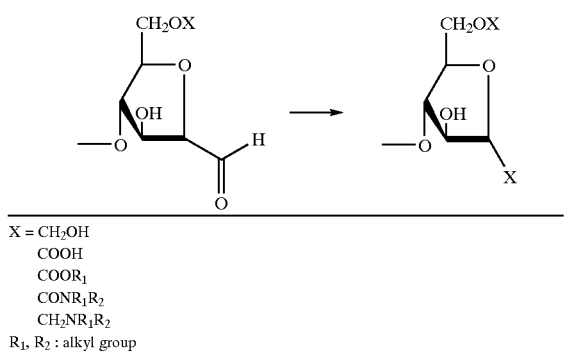

X = CH$_2$OH
COOH
COOR$_1$
CONR$_1$R$_2$
CH$_2$NR$_1$R$_2$
R$_1$, R$_2$ : alkyl group It is preferable that the low molecular weight modified heparins have an average molecular weight of 1,500~8,000, preferably 2,000~6,000. The modified heparin, original heparin, and low molecular weight modified heparins (for example, the low molecular modified heparins obtained in Examples 1–3 mentioned below) can be clearly distinguished from one another by means of high performance liquid chromatography (HPLC).

FIG. 1 shows results of HPLC, wherein a column, TSK, G-2000 SWXL (0.78 cm in diameter, 30 cm in length) prepared by Tosoh Corporation is used, and silicone resin fabricated beforehand to have a property of molecular sieve is filled in the column. The column has the ability to distinguish effectively compounds having a molecular weight of 500~20,000 when the compounds have generally linear molecular shapes like heparin.

The column was connected with a chromatopack C-R4A of HPLC 6A series made by Shimadzu Corporation. For the solvent was used 0.01M phosphate buffer solution of pH 7.3 containing 0.15M NaCl, which was developed at a rate of 0.5 ml per minute. The development was carried out at room temperature, and light of 210 nm was applied to the resultant eluates to detect heparin and its derivatives by measuring absorption of the light.

FIG. 1 is a graph in which the abscissa represents time (expressed by minutes) and the ordinate represents a relative intensity of absorption of light of 210 nm. In FIG. 1, a line including square marks shows behavior of heparin, a line including circle marks shows behavior of the modified heparin (which was obtained in Reference Example 2), a line including triangle marks shows behavior of the low molecular weight heparin (which was obtained in Reference Example 1) and a thick line including no marks shows behavior of the low molecular weight modified heparins (which were obtained in Examples 1, 2 and 3). The low molecular weight modified heparin is eluted in the area of molecular weight of about 1,500~8,000. As shown in FIG. 1, the low molecular weight modified heparins can be clearly distinguished from the original heparin and modified heparins. In addition, in FIG. 1, the modified heparin obtained in Reference Example 2 behaves as if it were a compound having somewhat lower molecular weight. However, it is assumed that this was caused by the probable facts that molecular shape of the modified heparin was slightly curved due to opening of ring structure in hexuronic acid. A peak observed at an elution time of 22 minutes shows existence of the salts.

Thus obtained modified heparin or low molecular modified heparin are separated and refined in appropriate methods known in itself and can be used as a remedying agent. For separating and refining can be used various methods such as precipitation methods using an organic solvent (alcohol, acetone etc.), various chromatography methods (for example, chromatographies using an ion exchange resin, active carbon, antibody or Sepharose) and refining methods by means of molecular sieves.

In the invention, both the modified heparin which was not depolymerized and was obtained in Reference Example 2, and the modified heparin which was depolymerized to have low molecular weights can be used as the agent for remedying skin ulcer. However, it is preferable to use the depolymerized modified heparin.

In case wherein heparin is depolymerized by a hydrolysis method, a product is obtained having L-threonic acid as an aglycon of aminosugar at the reducing terminal thereof, and aminosugar at the non-reducing terminal thereof, and in case wherein heparin is depolymerized by deaminative degradation, a product is obtained having 2,5-anhydro-D-mannose at the reducing terminal thereof and uronic acid at the non-reducing terminal thereof.

In the invention, the modified heparin and low molecular weight modified heparin (hereinafter both are collectively referred to as a heparin derivative) can be used as they are or after they were changed into salts thereof. The salts may have whichever forms, if the salts may be admitted pharmacologically. For example, the salts may be formed with organic acids such as acetic acid or inorganic acids such as hydrochloric acid. The salts may be formed by changing an acid group such as a sulfate residue in the heparin derivative into an alkali or alkaline earth metal salt. Also the heparin derivative may be a single compound or a mixture thereof.

The heparin derivative in the invention is effective for remedying various skin ulcers, for example, destruction, deficit etc. of skin caused by necrosis, desquamation, melting etc. of skin, more particularly, skin ulcers caused by wounds, decubitus, scalding, frostbite, or operation wounds, and skin infections (e.g. skin mycosis, psoriasis, varicella, tinea pedis, tinea corporis, pimple etc.).

The heparin derivative according to the invention can be administered parenterally or perorally as the agent for remedying skin ulcers. Preferably, it is administered parenterally. In case of parenteral administration, it may be used in the form of percutaneous administration drugs, that is, it may have any forms if it can be applied directly to affected parts of skin. It may be in the form of drugs able to provide active ingredients percutaneously, preferably, patch, cataplasm, ointment (including cream), plaster, tape, lotion, liquid, suspension, emulsion, aerosol (including sprayed materials) and so on. Applying articles such as patch, cataplast, tape, plaster, ointment and sprayed material are most preferable in respect that the active ingredients can be readily controlled.

The ointment, lotion, liquid, suspension, emulsion and aerosol can be prepared by blending the active ingredients with solvent, suspending agent, emulsifier, aerosol and base, respectively, which are known per se. At this time, antiseptics (for example, ethyl p-hydroxybenzoate, benzalkonium chloride etc.) may be further added, if desired.

Also the patch, cataplast, plaster and tape can be prepared by using a base known in itself in the pharmaceutical field, forming a mixture of the base and the active ingredients, adding thereto antiseptics if desired, and making the mixture absorbed in or adhered to an appropriate carrier. For the carrier can be used a high polymer membrane (for example, polyethylene, ethylene-vinyl acetate copolymer, polyethylene terephthalate etc.), woven fabric, non-woven fabric, paper, aluminium foil etc. For adhesives for forming the patch, cataplast and tape can be used various adhesives belonging to polyalkylvinylether, polyalkylacrylate, polyisobutylene, natural rubber and synthetic rubber. Further, animal oil (for example, squalene or squarane), vegetable oil (for example, olive oil or jojoba oil), vaseline, lanolin etc. may be added in order to give appropriate plasticity and tackiness.

When percutaneous drugs are prepared, such as ointment, plaster, tape, patch, cataplast and so on, an ingredient for regulating percutaneous absorption can be added. This ingredient can include lipids and fat-soluble substances including phospholipid such as lecithin, solid paraffin, beeswax, carnauba wax, hardened castor oil, lanolin, Vaseline® (petroleum jelly), polyvinyl alcohol, polyvinyl pyrrolidone, polyethylene glycol, fatty acid glycerol ester, cholestrol, fatty acids having about 6–22 carbons, (for example, capric acid, caprylic acid, caproic acid, lauric acid, myristic acid, palmitic acid, stearic acid, arachidonic acid, etc.) and their salts, aliphatic alcohol having about 6–22 carbons (for example, n-octyl alcohol, n-cetyl alcohol, stearyl alcohol etc.), silicone resin, and low aliphatic alcohol (for example, ethanol, isopropyl alcohol etc.). Of course, the active ingredients may be used alone or together with more than two of these bases.

The solvent can be water, low aliphatic alcohols (for example, ethanol, etc.), alkane diol having about 2–6 carbons (for example, glycol, etc.), and alkane triol having about 3–7 carbons (for example, glycerol). The suspending agent and emulsifier can be gum arabic, carboxymethyl cellulose, methyl cellulose, sodium alginate, etc. The base of the ointment, tape, patch and cataplasm can be Vaselineg (petroleum jelly), solid paraffin, vegetable oil, mineral oil, lanolin, wax, macrogol, etc. The base of plaster can be beeswax, paraffin, macrogol, glycerol ester of fatty acid, etc.

For a spraying agent can be used incombustible liquefied gas (for example, Freon 11, Freon 12, Freon 13 etc.).

In case of oral administration, the heparin derivative may be administered in the form of tablet, capsule, powder, granule, syrup, emulsion and suspension, which can be made according to the conventional methods.

An amount of the heparin derivative contained in the agent for remedying skin ulcer according to the invention is not limited and can be varied within the range wherein the agent can exhibit desirable remedying effects. The amount is dependent on the object, whichever it may be human or animal, to which the agent is administered, and also on the kind of diseases and the degree of diseases. For example, the amount of heparin derivative, acting as the active ingredient, contained in the agent for remedying decubitus according to the invention is approximately 0.001~30%, preferably approximately 0.01~10%, more preferably approximately 0.05~5% by weight of the total weight of the percutaneous drug, and in case of the patch, plaster, tape etc., an amount of heparin derivative per unit area is approximately 0.1 mg~200 mg/cm$^2$, preferably approximately 1~mg 20 mg/cm$^2$. Administration frequency is varied dependent on the kind and conditions of diseases. For example, the percutaneous application or administration is made from once to several times per day, and the application or administration is continued for more than two days.

The agent for remedying skin ulcer according to the invention may comprise other pharmaceuticals as an effective ingredient so long as the agent and other pharmaceuticals do not deteriorate their mutual remedying effects. The other pharmaceuticals may be any one, if it does not hinder the effects of the agent for remedying skin ulcer, and include, for example, various cell growth factors, cytokines or cell adhesion molecules (preferably transforming growth factor β, vasoendothelial cell growth factors, fibroblast growth factors or hepatocyte growth factors), various antibiotics (antibiotic agents, antifungal agents, antiviral agents etc.) various steroids, anti-inflammatory agents, anti-allergic agents, anti-histamic agents etc.

For lipids can be used various compounds, for example, phospholipids, preferably lecithin, and for fat-soluble substances can be used, for example, animal oils (e.g. squalene, squarane etc.), vegetable oils (e.g. olive oil, jojoba oil etc.), solid paraffin, beeswax, carnauba wax, hardened castor oil, lanolin, vaseline, polyvinyl alcohol, polyvinyl pyrrolidone, polyethyleneglycol, fatty acid glycerol ester, cholesterol, aliphatic carboxylic acid having about 6~22 carbons (e.g. capric acid, caprylic acid, caproic acid, lauric acid, myristic acid, palmitic acid, stearic acid, arachidonic acid etc.) and their salts, aliphatic alcohol having about 6~22 carbons (e.g. n-octyl alcohol, n-cetyl alcohol, stearyl alcohol etc.), preferably vaseline, polyethylene glycol, and aliphatic alcohol having about 6~22 carbons (e.g. n-octyl alcohol, n-cetyl alcohol, stearyl alcohol etc.), more preferably vaseline, polyethylene glycol and stearyl alcohol.

The agent for remedying skin ulcer according to the invention is very low in toxicity, and in case wherein the agent has been administered for a long period, either side effects or toxicity are hardly recognized. Therefore, the percutaneous drugs containing the heparin derivative according to the invention can be administered in safety for remedying the skin ulcer mentioned above, especially for remedying decubitus.

The drugs characterized by comprising the heparin derivative according to the invention can be simply and easily administered to patients, and when used for remedying decubitus, the drugs can reduce greatly the burden of patients and nurses not only in hospitals but also at home.

The invention is fully explained below by way of Reference Examples, Examples and Experiments. However, these are offered only for illustrative purposes, and do not limit the invention.

MANNERS OF EMBODIMENTS

Reference Example 1

One gram of porcine heparin was dissolved in 12.5 ml of distilled water, and thereto was added 1.25 ml of 5% sodium nitrite aqueous solution at room temperature. Then thereto was added 1.25 ml of 33% acetic acid aqueous solution, and the resultant solution was stirred for 50 minutes at room temperature to form a reaction solution. To the reaction solution were added 4 ml of 1M sodium carbonate aqueous solution and 1 ml of 1M sodium hydroxide aqueous solution in this order, and pH of the reaction solution was adjusted to 9.0. Thereto was further added 0.3 ml of 0.01M sodium hydroxide aqueous solution containing 0.25M sodium borohydride, and the resultant solution was allowed to stand for 30 minutes at 50° C. Then by adding glacial acetic acid thereto excessive sodium borohydride was decomposed, and subsequently the solution was passed through a column of Sephadex G-25 which had been equilibrated with 0.3M sodium acetate solution. The resultant high molecular weight fractions were concentrated under reduced pressure, and then by adding ethanol thereto an aimed product was precipitated. The precipitate was collected by filtration and dried to obtain about 0.9 g of low molecular weight heparin which had some anticoagulant activity.

Bovine heparin was subjected to similar operations and a low molecular weight heparin could be obtained which had some anticoagulant activity. Thus obtained low molecular weight heparin was subjected to HPLC analysis, in which it showed behavior as indicated by the line including triangle marks in FIG. 1.

Reference Example 2

One gram of porcine heparin was dissolved in 20 ml of 0.05M acetate buffer solution (pH 5.0) containing 0.1M sodium periodate, and the resultant solution was allowed to stand in the dark for 72 hours at 4° C. By adding glycerol thereto excess periodate was decomposed, and then the resultant solution was dialyzed against distilled water for three days at about 5° C., using a semipermeable membrane for use in dialysis (manufactured by Spectrum Co., Code Number 530-3518, MW500cut). The dialyzed solution was subjected to lyophilization, and the resultant product was dissolved in 0.25M sodium bicarbonate aqueous solution (pH 9.5) containing 0.2M sodium borohydride to make a 10% solution. The solution was allowed to stand for 3 hours at 4° C. By adding glacial acetic acid to the solution excess sodium borohydride was decomposed, and the solution was adjusted to have pH 5, and allowed to stand for 30 minutes. Subsequently the solution was neutralized with 0.1M sodium hydroxide aqueous solution. The resultant solution was again dialyzed against distilled water at about 5° C. for 3 days, using the semipermeable membrane for use in dialysis, and then the resulting solution was subjected to lyophilization to obtain 0.85 g of lyophilized product of modified heparin.

Bovine heparin was treated in similar manners and a modified heparin according to the invention could be obtained.

Thus obtained modified porcine heparin was subjected to HPLC analysis, in which it showed behavior as indicated by the line including circle marks in FIG. 1, in which the modified heparin behaved as if it were of slightly lower molecular weight, when compared with the original heparin. However, it is considered that this was probably caused by deformation in molecule of the modified heparin, because any changes in molecular weight cannot occur in the modification process mentioned above.

Example 1

One gram of the low molecular weight heparin obtained from porcine heparin by the method described in Reference Example 1 was dissolved in 0.05M acetic acid buffer solution (pH 5.0) containing 20 ml of 0.1M sodium periodate, and the resultant solution was allowed to stand in the dark for 72 hours at 4° C. By adding glycerol to the solution excess periodate was decomposed and then the solution was dialyzed against distilled water for 3 days at about 5° C., using a semipermeable membrane for use in dialysis (manufactured by Spectrum Co., Code Number 530-3518, MW500cut). The dialyzed solution was subjected to lyophilization, and the resultant product was dissolved in 0.25M sodium bicarbonate aqueous solution (pH 9.5) containing 0.2M sodium borohydride to make a 10% solution. The solution was allowed to stand for 3 hours at 4° C. By adding glacial acetic acid thereto excessive sodium borohydride was decomposed, thereafter the solution was adjusted to have pH 5.0 and allowed to stand for 30 minutes. Subsequently the solution was neutralized with 0.1M sodium hydroxide aqueous solution. The resultant solution was again dialyzed against distilled water at about 5° C. for 3 days, using the semipermeable membrane for use in dialysis, and then the resultant solution was subjected to lyophilization to obtain 0.7 g of lyophilized product, which was a low molecular weight modified heparin according to the invention which has no anticoagulant activity.

Bovine heparin was treated in similar manners, and a low molecular weight modified heparin according to the invention could be obtained.

Thus obtained low molecular weight modified porcine heparin was subjected to HPLC analysis, in which it showed such behavior as indicated by a thick line including no mark in FIG. 1, in which it is clear that the low molecular weight modified heparin had a lower molecular weight when compared with the original heparin and the modified heparin obtained in Reference Example 2. The molecular weight is seemingly in the range from about 1,500~8,000.

Example 2

One gram of porcine modified heparin obtained by the method described in Reference Example 2 was dissolved in 20 ml of 0.1M hydrochloric acid aqueous solution, and the resultant solution was carefully adjusted to have pH 2. The solution was heated rapidly to 60° C., and allowed to stand for about 1 hour. Immediately thereafter while being ice-chilled, the solution was neutralized with 0.1M sodium hydroxide aqueous solution, and then dialyzed against distilled water for 3 days at about 5° C., using a semipermeable membrane for use in dialysis (manufactured by Spectrum Co., Code Number 530-3518, MW500Cut). The dialyzed solution was lyophilized to obtain 0.7 g of a low molecular weight modified heparin according to the invention.

Bovine modified heparin was treated in similar manners, and a low molecular weight modified heparin according to the invention could be obtained.

Thus obtained low molecular weight modified porcine heparin was subjected to HPLC analysis, in which it showed such behavior as indicated by a thick line including no mark in FIG. 1, and the behavior was the same as that of the low molecular weight modified heparin obtained in Example 1.

Example 3

One gram of porcine modified heparin obtained by the method described in Reference Example 2 was dissolved in 12.5 ml of distilled water, and thereto was added 1.25 ml of 5% sodium nitrite aqueous solution. Then while being stirred, thereto was added 1.25 ml of 33% acetic acid aqueous solution and the resultant solution was further stirred for 50 minutes at room temperature. Thereto were added 4 ml of 1M sodium carbonate aqueous solution and 1 ml of 1M sodium hydroxide aqueous solution in this order, and the resultant solution was adjusted to have pH 9.0. Thereto was added 0.3 ml of 0.01M sodium hydroxide aqueous solution containing 0.25M sodium borohydride, and the resultant solution was allowed to stand for 30 minutes at 5° C. Subsequently, by adding glacial acetic acid thereto excessive sodium borohydride was decomposed, and then the resultant solution was either passed through a column filled with Sephadex G-25 equilibrated with 0.3M sodium acetate aqueous solution, or dialyzed in the same manners as in Examples 1 and 2. The liquid which had passed through the column (fractions containing higher molecular weight compounds), or the dialyzed solution was concentrated, and thereafter by adding ethanol thereto a low molecular weight modified heparin was precipitated. The precipitate was dried to obtain 0.9 g of a dried product.

Bovine modified heparin was treated in the same manners, and a low molecular weight modified heparin could be obtained.

The low molecular weight modified porcine heparin obtained herein was subjected to HPLC analysis, in which it showed such behavior as indicated by a thick line including no mark, and the behavior was seemingly the same as that of the low molecular weight modified heparins obtained in Examples 1 and 2.

Example 4

Below mentioned compounds were mixed as described below.

| The low molecular weight modified heparin obtained in any of Examples 1 ~ 3 | 1 part by weight |
|---|---|
| Stearyl alcohol | 33 parts by weight |
| Propylene glycol | 33 parts by weight |
| Polyalkylvinyl ether | 33 parts by weight |

The low molecular weight modified heparin was mixed with propylene glycol, then stearyl alcohol was added thereto, and the resultant mixture was blended and kneaded to form an ointment material, to which was added and blended polyalkylvinylether acting as a tackifier to form an ointment.

The ointment was applied on a release liner made of a polyester resin to form an ointment layer of about 0.1 mm in thickness, thereafter the ointment layer was transferred to a polyester film to obtain a plaster containing 1%(W/W) low molecular weight modified heparin.

The plaster was cut to a size fit for an affected part, and can be used for therapy.

Example 5

Below mentioned compounds were mixed as described below.

| The low molecular weight modified heparin obtained in any of Examples 1 ~ 3 | 1 part by weight |
|---|---|
| Vaseline | 69 parts by weight |
| Polyalkylvinyl ether | 30 parts by weight |

The compounds were mixed intimately to form a homogeneous ointment, which was then applied on a flexible gauze (woven fabric) to obtain a plaster having an agent layer of about 0.1 mm in thickness and containing 1%(W/W) low molecular weight modified heparin.

The plaster was cut to a size fit for an affected part, and can be used for therapy.

Example 6

| The low molecular weight modified heparin obtained in any of Examples 1 ~ 3 | 1 part by weight |
|---|---|
| Vaseline | 99 parts by weight |

These compounds were mixed intimately to obtain a homogeneous ointment. The ointment was applied to an affected part just to cover the part in an appropriate thickness, and can be used for therapy.

Experiment 1

Mouse (including diabetic mouse), rat, guinea pig and mini-pig were used to test the materials described in the present invention for remedying effect for skin ulcer. This experiment is in the case wherein the material was applied to the quinea pig.

Skin ulcers having a diameter of 8 mm and a depth of 2~3 mm were formed at three spots on each side of back bone of quinea pigs weighing about 200~300 g using a metal punch. An ointment was prepared by adding the low molecular weight modified heparin obtained in any of Examples 1~3 to vaseline in a ratio of the heparin 1 mg/the vaseline 1 g and mixing intimately the resulting mixture, and 1 g of the ointment was applied to three skin ulcers on one side, and for the purpose of comparison 1 g of vaseline containing no drug was applied to three skin ulcers on the other side. The whole back of each of the quinea pigs was covered with a transparent dressing film (10 cm×12 cm), which was fixed by a flexible tape.

Effectiveness of the agent was assayed by two methods, one of which is (i) comparison of the number of days up to complete closure of the ulcers and the other is (ii) analyzing tissue specimen of the ulcers after it had been stained (with hematoxylin-eosin).

As the results, it was found that (i) as seen from FIG. 2, 22±2 days were required for apparent healing (skin surface closure) when vaseline alone was used. However, significantly shortened periods such as only 16±2 days were required for the apparent healing, when any one of the low molecular weight modified heparins obtained in Examples 1~3 were used. When the modified heparin in Reference Example 2 was used, 17±2 days were required for apparent healing, and these results were at a glance equal to those in case wherein the low molecular weight modified heparins obtained in any of Examples 1~3 were used. However, when the tissues were dissected and inspected, the equality was found to be nothing but apparent phenomena. (ii) when tissue specimens were taken on the 11th day and stained, the following differences were found: When vaseline alone was used, the specimen did not show restoration of skin surface and skin epithelization did not occur as shown in FIG. 4. In contrast, when the low molecular weight modified heparins obtained in any of Examples 1~3 were used, both corneum and appendage structures were formed and almost complete skin epithelization was recognized as shown in FIG. 5. On the other side, when the modified heparin obtained in Reference Example 2 was used, the healing effect was considerably inferior to that when the low molecular weight modified heparins were used, because as shown in FIG. 6, both corneum and appendage structures were insufficiently formed, although the skin surfaces were seemingly restored. From these results it was confirmed that the low molecular weight modified heparins according to the invention were especially effective in remedying skin ulcers.

Experiment 2

In the same manners as in Experiment 1, heparin and low molecular weight modified heparin obtained in Reference Example 1 having anticoagulant activity were tested for remedying skin ulcers. As the results no significant effects were found in any of two experiments, as far as days up to complete remedy (FIG. 3) and skin epithelization in tissue specimens are concerned.

INDUSTRIAL APPLICABILITY

The modified heparins and low molecular weight modified heparins according to the present invention have excellent effects for remedying skin ulcers such as skin wounds, especially decubitus ulcers, and also have such low toxicity that they give neither side effect nor toxicity even if administered for a long term, so that they are useful as an agent for remedying skin ulcers.

What is claimed is:

1. A composition for treating skin ulcer comprising an effective amount of a modified heparin for remedying skin ulcer in a pharmaceutically acceptable carrier selected from the group consisting of petroleum jelly and polyalkylvinylether for enhancing cutaneous absorption, wherein the modified heparin is prepared by oxidizing heparin with periodate and then reducing the resultant product with borohydride; and the modified heparin is substantially deprived of anticoagulant activity but retains an ability to bind to cell growth factors, cytokines and cell adhesion molecules.

2. A composition for treating skin ulcer comprising an effective amount of a modified heparin for remedying skin ulcer in a pharmaceutically acceptable carrier selected from the group consisting of petroleum jelly and polyalkylvinylether for enhancing cutaneous absorption, wherein the modified heparin has an average molecular weight of about 1,500 to 8,000; the modified heparin is prepared by oxidizing heparin with periodate, and then reducing the resultant product with borohydride, and subsequently depolymerizing the reduced heparin; and the modified heparin is substantially deprived of anticoagulant activity but retains an ability to bind to cell growth factors, cytokines and cell adhesion molecules.

3. A composition for treating skin ulcer comprising an effective amount of a modified heparin for remedying skin ulcer in a pharmaceutically acceptable carrier selected from the group consisting of petroleum jelly and polyalkylvinylether for enhancing cutaneous absorption, wherein the modified heparin is prepared by depolymerizing heparin, oxidizing the depolymerized heparin with periodate, and then reducing the oxidized heparin with borohydride; and is substantially deprived of anticoagulant activity but retains an ability to bind to cell growth factors, cytokines and cell adhesion molecules.

4. The composition for treating skin ulcer according to claim 3, wherein the composition is a percutaneous composition and the modified heparin has an average molecular weight of about 1,500 to 8,000.

5. A composition for treating skin ulcer comprising an effective amount of a modified heparin for remedying skin ulcer in a pharmaceutically acceptable carrier, wherein the modified heparin:

has an average molecular weight of about 1,500 to 8,000;

is prepared by oxidizing heparin with periodate, and then reducing the resultant product with borohydride, subsequently depolymerizing the reduced heparin, and further modifying active groups located at terminals of the depolymerized heparin to a member selected from the group consisting of carboxyl group, ester of carboxyl group, amide of carboxyl group, and Schiff bases; and is substantially deprived of anticoagulant activity but retains an ability to bind to cell growth factors, cytokines and cell adhesion molecules.

6. The composition for treating skin ulcer according to claim 1, wherein the modified heparin is present in an amount of 0.001 to 30% by weight of the composition.

7. The composition for treating skin ulcer according to claim 2, wherein the modified heparin is present in an amount of 0.001 to 30% by weight of the composition.

8. The composition for treating skin ulcer according to claim 3, wherein the modified heparin is present in an amount of 0.001 to 30% by weight of the composition.

9. The composition for treating skin ulcer according to claim 4, wherein the modified heparin is present in an amount of 0.001 to 30% by weight of the composition.

10. The composition for treating skin ulcer according to claim 5, wherein the pharmaceutically acceptable carrier is a member selected from the group consisting of petroleum jelly and polyalkylvinyleither, and the modified heparin is present in an amount of 0.001 to 30% by weight of the composition.

* * * * *